(12) United States Patent
Bihler et al.

(10) Patent No.: US 11,610,703 B2
(45) Date of Patent: Mar. 21, 2023

(54) DIFFUSION BARRIER FOR IMPLANTABLE ELECTRODE LEADS

(71) Applicant: BIOTRONIK SE & Co. KG, Berlin (DE)

(72) Inventors: Eckardt Bihler, Winterthur (CH); Marc Hauer, Uster (CH)

(73) Assignee: BIOTRONIK SE & Co. KG, Berlin (DE)

( * ) Notice: Subject to any disclaimer, the term of this patent is extended or adjusted under 35 U.S.C. 154(b) by 960 days.

(21) Appl. No.: 16/429,892

(22) Filed: Jun. 3, 2019

(65) Prior Publication Data
US 2019/0392964 A1    Dec. 26, 2019

(30) Foreign Application Priority Data
Jun. 20, 2018    (DE) .................... 10 2018 114 801.1

(51) Int. Cl.
*B29C 65/00* (2006.01)
*H01B 13/06* (2006.01)
(Continued)

(52) U.S. Cl.
CPC .............. *H01B 13/06* (2013.01); *A61N 1/05* (2013.01); *A61N 1/3754* (2013.01); *B29C 65/34* (2013.01); *B29C 66/742* (2013.01); *B32B 27/08* (2013.01); *B32B 37/06* (2013.01); *H01B 7/048* (2013.01); *H01B 7/0838* (2013.01); *H01B 13/0013* (2013.01); *H01B 13/0016* (2013.01); *H01B 13/0036* (2013.01); *B29C 65/342* (2013.01);
(Continued)

(58) Field of Classification Search
CPC .............. B29C 65/342; B29C 65/3444; B29C 65/3456; B29C 65/3476
See application file for complete search history.

(56) References Cited

U.S. PATENT DOCUMENTS 4,781,304 A * 11/1988 Lapeyre ............... B65D 17/462
                                                    220/280
5,312,442 A *  5/1994 O'Phelan ............. A61N 1/3956
                                                    607/5
(Continued)

FOREIGN PATENT DOCUMENTS

DE    19916494 A1    10/2000
DE    69705174 T2     5/2002
(Continued)

OTHER PUBLICATIONS

German Search Report for German Case No. DE 10 2018 114 801.1, dated Oct. 26, 2018 (7 pages).

*Primary Examiner* — Philip C Tucker
*Assistant Examiner* — Nickolas R Harm
(74) *Attorney, Agent, or Firm* — Buchanan Ingersoll & Rooney PC

(57) ABSTRACT

A process for producing an electrical conductor structure that involves embedding at least one metallic conductor track and at least one heating conductor in an electrically insulating substrate, and producing an electric current in the heating conductor so that a first layer of the substrate and a second layer of the substrate fuse in an area surrounding the heating conductor, to seal an interface between the two layers. A conductor structure is also disclosed, in particular in the form of an implantable electrode lead.

15 Claims, 3 Drawing Sheets

(51) Int. Cl.
*H01B 7/04* (2006.01)
*H01B 7/08* (2006.01)
*H01B 13/00* (2006.01)
*A61N 1/375* (2006.01)
*B29C 65/34* (2006.01)
*B32B 27/08* (2006.01)
*B32B 37/06* (2006.01)
*A61N 1/05* (2006.01)
*B29L 31/00* (2006.01)

(52) U.S. Cl.
CPC ...... *B29C 65/3444* (2013.01); *B29C 65/3456* (2013.01); *B29C 65/3476* (2013.01); *B29L 2031/753* (2013.01); *B32B 2535/00* (2013.01)

(56) References Cited

U.S. PATENT DOCUMENTS

| | | | | |
|---|---|---|---|---|
| 5,389,184 | A * | 2/1995 | Jacaruso | B29C 66/7394 219/544 |
| 6,519,835 | B1 * | 2/2003 | Von Arx | B29C 70/885 219/544 |
| 9,162,064 | B2 * | 10/2015 | Faltys | A61N 1/3606 |
| 2001/0050278 | A1 * | 12/2001 | Chenault | B29C 66/9121 219/535 |
| 2002/0088111 | A1 * | 7/2002 | Von Arx | H05B 3/28 29/613 |
| 2006/0271141 | A1 * | 11/2006 | MacDonald | A61N 1/04 607/119 |
| 2010/0100095 | A1 | 4/2010 | Mcclurken et al. | |
| 2010/0241229 | A1 * | 9/2010 | Baehre | A61B 17/864 252/500 |
| 2011/0190849 | A1 * | 8/2011 | Faltys | A61N 1/3756 607/50 |
| 2012/0188042 | A1 * | 7/2012 | Claude | B29D 23/001 336/90 |
| 2017/0056675 | A1 * | 3/2017 | Bortolin | A61B 5/318 |
| 2017/0173860 | A1 * | 6/2017 | Grgac | B29C 66/131 |
| 2018/0068759 | A1 * | 3/2018 | Bihler | H05K 1/0283 |

FOREIGN PATENT DOCUMENTS

| | | |
|---|---|---|
| EP | 1097797 A1 | 5/2001 |
| EP | 0823321 B1 | 6/2001 |
| JP | 58059050 A | 4/1983 |

* cited by examiner

DIFFUSION BARRIER FOR IMPLANTABLE ELECTRODE LEADS

CROSS-REFERENCE TO RELATED APPLICATIONS

This patent application claims the benefit of and priority to co-pending German Patent Application No. DE 2018 114 801.1, filed on Jun. 20, 2018 in the German Patent Office, which is hereby incorporated by reference in its entirety.

TECHNICAL FIELD

The present invention relates to a process for producing an electrical conductor structure, in particular in the form of an implantable electrode lead, in particular the form of a ribbon cable, and such a conductor structure.

BACKGROUND

When multilayer substrates made of thermoplastic materials are laminated, the temperature and the pressure must be selected in such a way to produce good adhesion between the layers. At the same time, care must be taken that the structure of the substrate remain intact and is not become blurred. This limits the temperatures and pressures that can be used. As a consequence, the interfaces do not completely disappear, and along these interfaces moisture can penetrate, which reduces the insulation resistance between different conductor tracks and the surrounding body fluid and represents a limit for the in vivo service life that can be achieved. European Patent No. 823 321 B1 describes a heating conductor in a cover of a battery housing, this wire being intended to fuse together the two thermoplastic components. United States Publication No. 2010/100095 also mentions the possibility of connecting a liquid crystal polymer ("LCP") with a housing by hot caulking, a press fit, or ultrasonic welding.

The present invention is directed at overcoming one or more of the above-mentioned problems. Starting from this prior art, this invention therefore has the goal of creating a process for producing an electrical conductor structure, in particular in the form of an implantable electrode lead, in particular in the form of a ribbon cable, and such a conductor structure, in which the moisture penetration along an interface between two layers of the laminated structure is reduced, in particular in order to increase the in vivo service life of the conductor structure.

SUMMARY

At least this goal is achieved by a process having the features of claim 1 and a conductor structure having the features of claims 13 and 14. Advantageous embodiments of these aspects of this invention are indicated in the subordinate claims and are described in detail below.

Claim 1 discloses a process for producing an electrical conductor structure that involves embedding at least one metallic conductor track and at least one heating conductor in an electrically insulating substrate, and producing an electric current in the heating conductor so that a first layer of the substrate and a second layer of the substrate fuse in an area surrounding the heating conductor, to seal an interface between the two layers.

Fusing the two layers in the area surrounding the at least one heating conductor interrupts the interface at this place, and thus the at least one heating conductor can prevent or substantially reduce a migration of ions along the interface.

Thus, the present invention makes it possible to reduce the penetration of moisture within conductor structures, in particular implantable electrode leads, made from multiple laminated layers of, e.g., LCP, which advantageously substantially increases the service life of the electrode lead/conductor structure.

One embodiment of the inventive process provides that the at least one conductor track and the at least one heating conductor be embedded in the substrate by the at least one conductor track and the at least one heating conductor being put onto the first layer and the second layer being connected (e.g., by material bonding) with the first layer, forming the interface. To connect the first layer with the second layer, e.g., the two layers consisting of plastic are heated to a temperature of 240° to 350° C. and connected together at a pressure of 5 to 50 bar.

The at least one conductor track and/or the at least one heating conductor can be embedded in a surface of the first layer, in particular in such a way that at least one surface of the at least one conductor track is exposed and/or in such a way that at least one surface of the heating conductor is exposed (and, in particular, in such a way that at least sections of it run on or along the interface after application of the second layer).

Furthermore, according to one embodiment of the inventive process, the at least one heating conductor is arranged so that it encircles the at least one conductor track along the interface, i.e., encloses the at least one conductor track with respect to the interface.

One embodiment of the inventive process further provides that the at least one heating conductor be embedded in the substrate and/or applied to the first layer in such a way that it extends along one edge of the substrate, the distance of the heating conductor to an edge of the substrate or to an edge of the first layer preferably being in the range from 0 μm to 1,000 μm.

One embodiment of the inventive process further provides that the first layer consist of a first plastic, and that the second layer consist of a second plastic.

One embodiment of the inventive process further provides that the first plastic have a lower melting point than the second plastic.

For example, according to one embodiment, the first plastic can have a melting point less than or equal to 280° C. Furthermore, according to one embodiment, the second plastic can have a melting point less than or equal to 330° C. Furthermore, according to one embodiment, the heating conductor is heated to a temperature that is greater than the melting point of the second plastic, and is, in particular, less than or equal to 350° C.

In principle, the present invention can be applied to all thermoplastic polymers. In particular, in this invention, the first and the second plastics can be not only liquid crystal polymer (LCP) but also polyetheretherketone (PEEK), a fluoropolymer (e.g., polyvinylidene fluoride (PVDF) or polytetrafluoroethylene (PTFE)), and their copolymers. Other possible materials for the first and the second plastics are polysulfones and polyethylethers.

One embodiment of the inventive process further provides that the at least one heating conductor be made from, or contain a biocompatible, conductive material. The heating conductor is preferably formed from or has one of the following materials: a biocompatible metal or a biocompatible alloy, metals such as, e.g., aluminum, magnesium, or iron, a noble metal such as, e.g., gold, platinum, titanium, an alloy having a metal or a noble metal such as, e.g., gold, platinum, titanium, tungsten, aluminum, magnesium, iron. The heating conductor can be applied by means of PVD (physical vapor deposition), e.g., photolithographically structured.

One embodiment of the inventive process further provides that a thickness of the at least one heating conductor (in particular in the direction normal to the interface) lie in the range from 10 nm to 50 μm, and/or that a width of the at least one heating conductor (especially in the direction along the interface) lie in the range from 1 μm to 1,000 μm.

One embodiment of the inventive process further provides that the at least one heating conductor be brought out of the substrate at two places, so that two contact sections of the at least one heating conductor protrude out of the substrate, a voltage being applied to the contact sections to produce the current in the heating conductor.

One alternative embodiment of the inventive process further provides that the at least one heating conductor have a ring conductor with an induction coil or an induction loop to couple in an alternating voltage or a ladder antenna to absorb RF radiation, current from an external source being produced in the heating conductor by inducing a voltage in the induction coil or in the induction loop or by coupling RF radiation into the antenna.

One embodiment of the inventive process further provides that the contact sections be removed after the two layers are fused in the said area surrounding the at least one heating conductor.

One embodiment of the inventive process further provides that the electrical conductor structure be an implantable electrode lead.

One embodiment of the inventive process further provides that at least one electrode contact be formed or arranged on the substrate to make contact with body tissue, the at least one electrode contact being connected in an electrically conductive manner with the at least one conductor track by means of a feedthrough.

One embodiment of the inventive process further provides that the electrical conductor structure or the implantable electrode lead be in the form of a ribbon cable.

Another aspect of this invention relates to a conductor structure that has been produced by the inventive process.

Another aspect of this invention relates to a conductor structure with at least one metallic conductor track, and with at least one heating conductor, the at least one conductor track and the at least one heating conductor being embedded in an electrically insulating substrate, and a first layer of the substrate being fused with a second layer of the substrate or being fusible with a second layer of the substrate by means of the heating conductor in an area surrounding the heating conductor, to seal an interface between the two layers of the conductor structure.

One embodiment of the inventive conductor structure provides that the conductor structure form an implantable electrode lead and/or be in the form of a ribbon cable, the electrode lead having, in particular, at least one electrode contact arranged on the substrate to make contact with body tissue, the electrode contact being connected with the at least one conductor track of the implantable electrode lead through a feedthrough.

Additional features, aspects, objects, advantages, and possible applications of the present invention will become apparent from a study of the exemplary embodiments and examples described below, in combination with the Figures, and the appended claims

DESCRIPTION OF THE DRAWINGS

The discussion below is intended to explain other features and embodiments of this invention on the basis of the Figures. The Figures are as follows.

DETAILED DESCRIPTION

Figure 1:
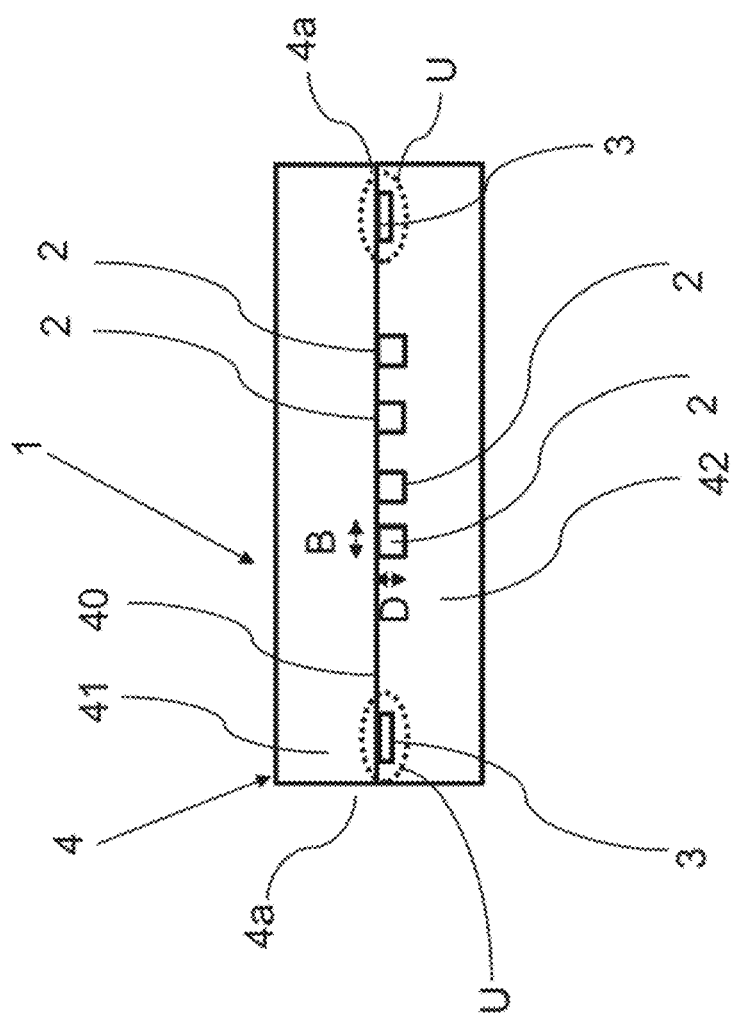
FIG. 1 shows a schematic sectional view of an embodiment of an inventive conductor structure.
Figure 2:
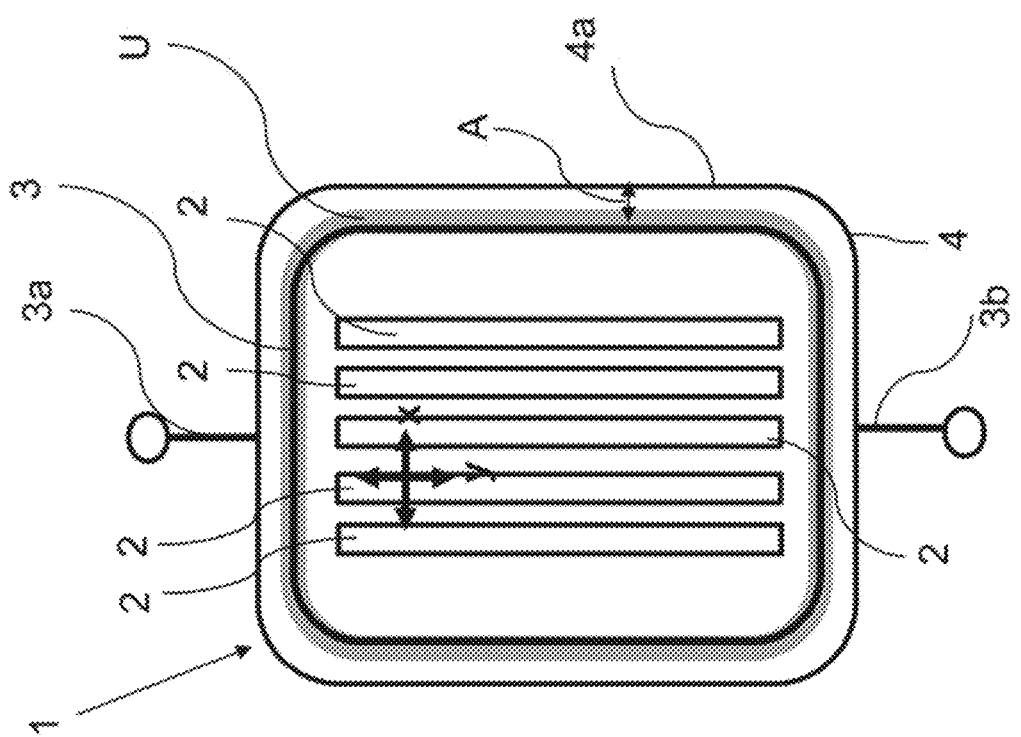
FIG. 2 shows a top view of the interface of the conductor structure according to FIG. 1.

FIG. 1 in connection with FIG. 2 shows an embodiment of an electrical conductor structure 1, which here is, e.g., an implantable electrode lead in the form of a ribbon cable. However, the present invention is also applicable to other conductor structures 1.

The conductor structure 1 has an electrically insulating substrate or insulation 4, which has a first layer 41 and a second layer 42. The conductor structure 1 has at least one conductor track 2, in this case, for example, multiple conductor tracks 2 being provided.

The conductor tracks 2 are embedded between the two layers 41, 42, each of the layers here being formed by films 41, 42 made of a liquid crystal polymer ("LCP"). This involves the conductor tracks 2 first being applied onto the first layer 41, which is shown in cross section in FIG. 1. The first plastic or LCP of the first layer 41 can be, for example, the material Ultralam® 3850 HT (Roger Corporation), which has a melting point of about 330° C. After the conductor tracks 2 are completed, the conductor tracks 2 are usually covered with a second layer 42 made of a second plastic, here, e.g., also an LCP. The covering is done by lamination under temperature and uniaxial pressure. The LCP of the second layer 42 can be, for example, the material Ultralam® 3908 (Roger Corporation), which has a lower melting point of about 280° C. The second layer 42 melts/softens as it is laminated on the first layer 41. The lamination of the mentioned materials involves the use of uniaxial pressures of 5 to 50 bar. The temperatures and pressures used in this process are preferably selected in such a way that the structures do not become too strongly blurred along the interface 40 in the XY-plane. As a consequence, an interface 40 between the layers 41, 42 does not completely disappear.

Soak tests with such structures have found that moisture-promoted ion migration can occur along the interface 40 arising between the two LCP layers 41, 42, and this ion migration reduces the resistance between the conductor tracks 2, and thus limits the life of the electrode lead 1. The lamination can also easily include foreign material, which then additionally promotes the migration.

To eliminate this problem, at least one heating conductor 3 is applied to the first layer 41 directly on the edge of the ribbon cable or of the conductor structure 1 before it is covered with the second layer 42. The at least one heating conductor 3 can, as shown in FIG. 2, encircle or enclose the conductor tracks in the plane of the interface. In particular, the at least one heating conductor can be applied by means of PVD so that it is photolithographically structured, it being possible for the thickness D of the heating conductor to be about 10 nm to 50 μm, according to an example. The heating conductor width B can be about 1 μm to 1,000 μm, according to an example. Furthermore, the distance A to the edge 4a of the substrate 4 or to the edge of the first layer 41 can be, for example, about 1 µm to 1,000 µm.

During the course of producing the ribbon cable or the conductor structure 1, the heating conductor 3, which can be made, e.g., of titanium, is used to produce Joule heat, and to accomplish this is it is connected with a suitably dimensioned current flow, so that the heating conductor 3 is heated to a temperature of, for example, over about 350° C. At this temperature, both LCP layers 41, 42 melt in the area U immediately along the heating conductor 3. The refusing of the LCPs 41, 42 in the area U surrounding the heating conductor 3 interrupts the interface 40 at this place, and the titanium conductor track can prevent or substantially reduce a migration of ions along the interface 40. This prevents displacement of the remaining areas and structures in the XY plane.

As can also be seen in FIG. 2, the at least one heating conductor 3 can be brought out of the ribbon cable 1 or out of the conductor structure 1 in at least two places, producing correspondingly exposed contact sections 3a, 3b of the heating conductor 3, to which a voltage can be applied to produce a current in the heating conductor 3, i.e., the heater current can be coupled in through the contact sections 3a, 3b. After that, the contact sections 3a, 3b are then cut off (e.g., with a laser), in particular in the context of separating the ribbon cable or conductor structures 1 from the production panel. The connections to the heating conductor 3 in the interface 40 that are left open at these places do not represent any problem if the conductor structure 1 is used in the human body, since titanium is a biocompatible metal, and the heating conductor 3 does not have any electrical connections inside the electrode lead 1. Since the resistance of the heating conductor 3 changes as a consequence of the temperature, this change in resistance can be used to control the heating process. Controlling the temperature/duration of the heating can control the size of the fusion zone U, and tailor it to the product design.

Figure 3:
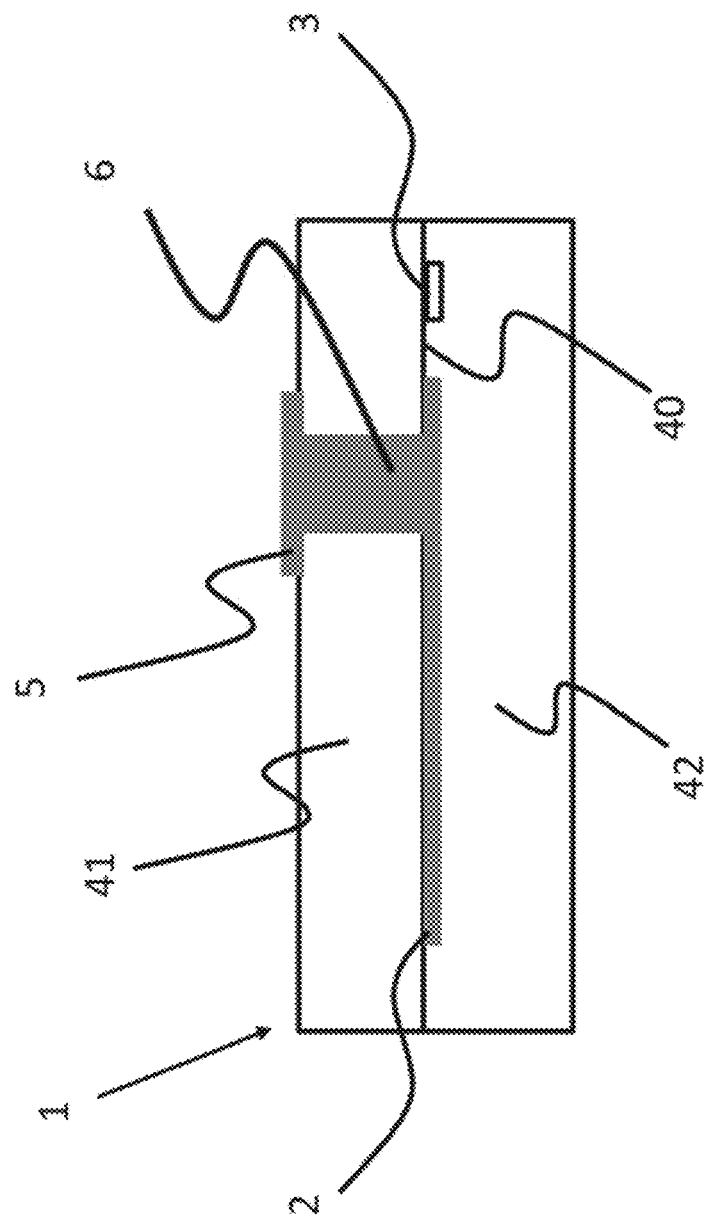
FIG. 3 shows a schematic sectional view of an embodiment of an inventive conductor structure with an electrode contact.

FIG. 3 shows an embodiment of an electrical conductor structure 1, which here is, e.g., an implantable electrode lead 1 in the form of a ribbon cable. The conductor track 2 shown as an example is embedded between the two layers 41, 42, each of the layers here being formed by films 41, 42 made of a liquid crystal polymer ("LCP"). The electrical conductor structure 1 or the electrode lead 1 shown has an electrode contact 5 arranged on the first layer 41 to make contact with body tissue, the electrode contact 5 being connected with the at least one conductor track 2 of the implantable electrode lead 1 through a feedthrough 6 that traverses the first layer 41. The feedthrough 6 can be in the form of a via 6, for example.

In principle, the present invention can be applied to all thermoplastic polymers. In particular, liquid crystal polymers (LCP), PEEK, or fluoropolymers (PVDF and PTFE), and their copolymers would also be suitable for applications in medicine.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. A process for producing an electrical conductor structure comprising:
    embedding at least one metallic conductor track and at least one heating conductor in an electrically insulating substrate, and
    producing an electric current in the at least one heating conductor so that a first layer of the substrate and a second layer of the substrate fuse in an area surrounding the at least one heating conductor, to seal an interface between the first layer and the second layer and seal the at least one metallic conductor track therebetween,
    wherein the at least one metallic conductor track is separate from and not connected to the at least one heating conductor.

2. The process according to claim 1, wherein the at least one conductor track and the at least one heating conductor are embedded in the substrate by the at least one conductor track and the at least one heating conductor being put onto the first layer and the second layer being connected by material bonding with the first layer, forming the interface.

3. The process according to claim 1, wherein the first layer consists of a first plastic, and the second layer consists of a second plastic.

4. The process according to claim 3, wherein the first plastic has a lower melting point than the second plastic.

5. The process according to claim 3, wherein the first plastic is or has one of the following substances: a thermoplastic polymer, a liquid crystal polymer, PEEK, a fluoropolymer, polyvinylidene fluoride (PVDF), polytetrafluoroethylene (PTFE).

6. The process according to claim 3, wherein the second plastic is one of the following substances or has one of the following substances: a thermoplastic polymer, a liquid crystal polymer, PEEK, a fluoropolymer, PVDF, PTFE.

7. The process according to claim 1, wherein the at least one heating conductor is formed from one of the following materials, or has one of the following materials: a biocompatible metal, a biocompatible alloy, metals including at least one of aluminum, magnesium, or iron, noble metals including at least one of gold, platinum, or titanium, and an alloy including at least one of gold, platinum, titanium, tungsten, aluminum, magnesium, or iron.

8. The process according to claim 1, wherein a thickness of the at least one heating conductor lies in the range from 10 nm to 50 µm, and/or a width of the at least one heating conductor lies in the range from 1 µm to 1,000 µm.

9. The process according to claim 1, wherein the at least one heating conductor is brought out of the substrate at two places, so that two contact sections of the at least one heating conductor protrude out of the substrate, and wherein a voltage being applied to the contact sections to produce the current in the at least one heating conductor.

10. The process according to claim 9, wherein the contact sections of the at least one heating conductor are removed after the first layer and the second layer are fused in the said area surrounding the at least one heating conductor.

11. The process according to claim 1, wherein the electrical conductor structure is in the form of a ribbon cable.

12. A process for producing an electrical conductor structure comprising:
    embedding at least one metallic conductor track and at least one heating conductor in an electrically insulating substrate, and
    producing an electric current in the at least one heating conductor so that a first layer of the substrate and a second layer of the substrate fuse in an area surrounding the at least one heating conductor, to seal an interface between the first layer and the second layer, wherein the electrical conductor structure is an implantable electrode lead.

13. A conductor structure produced by the process according to claim 1.

14. A conductor structure comprising:
- at least one metallic conductor track, and
- at least one heating conductor, the at least one conductor track and the at least one heating conductor being embedded in an electrically insulating substrate, and a first layer of the substrate being fused with a second layer of the substrate or being fusible with a second layer of the substrate by means of the at least one heating conductor in an area surrounding the at least one heating conductor, to seal an interface between the first layer and the second layer of the conductor structure and seal the at least one metallic conductor track therebetween,
- wherein the at least one metallic conductor track is separate from and not connected to the at least one heating conductor.

15. The conductor structure according to claim 14, wherein the conductor structure forms an implantable electrode lead and has at least one electrode contact arranged on the substrate to make contact with body tissue, the electrode contact being connected with the at least one conductor track through a feedthrough.

* * * * *